US00PP37440P2

(12) United States Plant Patent
van Swieten

(10) Patent No.: US PP37,440 P2
(45) Date of Patent: May 26, 2026

(54) ***PHALAENOPSIS* PLANT NAMED 'PHA379819'**

(50) Latin Name: *Phalaenopsis hybrida*
Varietal Denomination: PHA379819

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/329,263

(22) Filed: Sep. 15, 2025

(51) Int. Cl.
*A01H 6/62* (2018.01)
*A01H 5/02* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'PHA379819', characterized by its compact and upright plant habit; moderately vigorous growth habit and moderate growth rate; strong flowering stems; freely flowering habit with typically two inflorescences developing per plant, each inflorescence with numerous flowers; narrow to medium white-colored flowers; and good postproduction longevity.

2 Drawing Sheets

Figure 1:
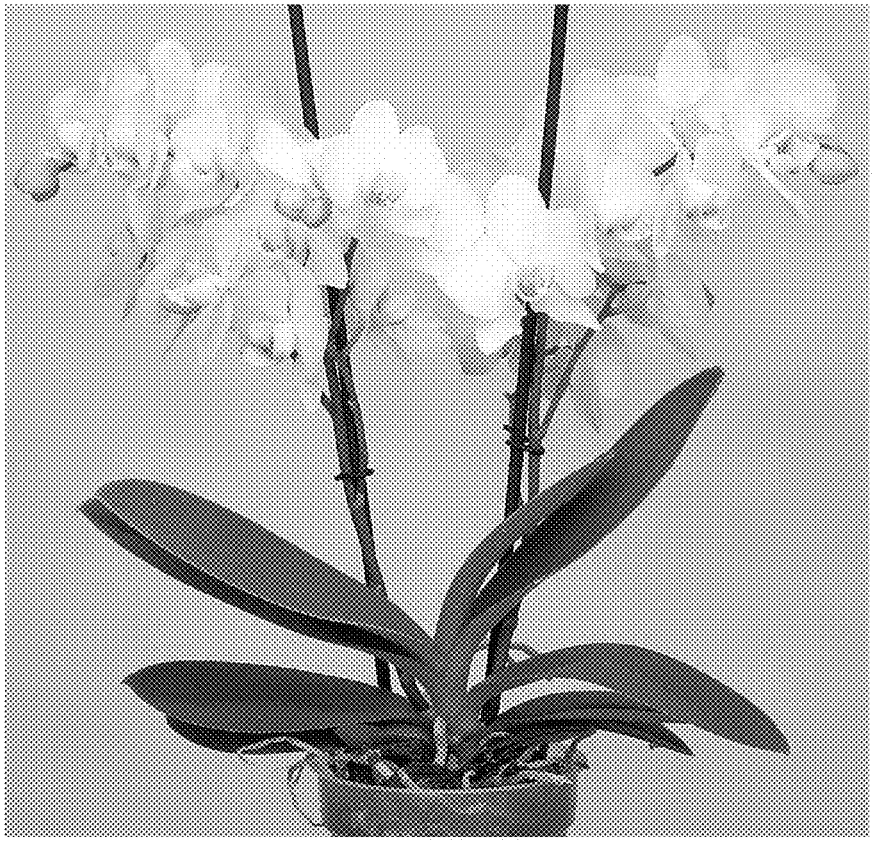

Botanical designation: *Phalaenopsis hybrida.*
Cultivar denomination: 'PHA379819'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Dec. 30, 2024, application number 2024/3258. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA379819'.

The new *Phalaenopsis* plant is a product of a planned breeding program conducted by the Inventor in Bleiswijk, The Netherlands. The objective of the breeding program is to develop new freely flowering *Phalaenopsis* plants with white-colored flowers.

The new *Phalaenopsis* plant originated from a cross-pollination in May, 2018 in Bleiswijk, The Netherlands of a proprietary breeding selection of *Phalaenopsis hybrida* identified as code number 12-051399-0002, not patented, as the female, or seed, parent with a proprietary breeding selection of *Phalaenopsis hybrida* identified as code number 13-057233-0001, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in December, 2020.

Asexual reproduction of the new *Phalaenopsis* plant by in vitro meristem propagation in a controlled environment in Bleiswijk, The Netherlands since December, 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA379819'. These characteristics in combination distinguish 'PHA379819' as a new and distinct *Phalaenopsis* plant:

1. Compact and upright plant habit.
2. Moderately vigorous growth habit and moderate growth rate.
3. Strong flowering stems.
4. Freely flowering habit with typically two inflorescences developing per plant, each inflorescence with numerous flowers.
5. Narrow to medium white-colored flowers.
6. Good postproduction longevity.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are erect to semi- erect in aspect whereas leaves of plants of the female parent selection are semi-erect in aspect.

2. Flowers of plants of the new *Phalaenopsis* are narrower than flowers of plants of the female parent selection.
3. Flowers of plants of the new *Phalaenopsis* are flat in lateral view whereas flowers of plants of the female parent selection are concave in lateral view.
4. The lateral lobes of the labella of plants of the new *Phalaenopsis* are more inwardly curved than the lateral lobes of the labella of plants of the female parent selection.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are erect to semi-erect in aspect whereas leaves of plants of the male parent selection are semi-erect to horizontal in aspect.
2. Petal apices of plants of the new *Phalaenopsis* are obtuse to broadly retuse whereas petal apices of plants of the male parent selection are slightly emarginate.

Plants of the new *Phalaenopsis* can be compared to plants of *Phalaenopsis hybrida* 'PHA1794396', not patented. In side-by-side comparisons, plants of the new *Phalaenopsis* differ primarily from plants of 'PHA1794396' in the following characteristics:

1. Dorsal sepals of plants of the new *Phalaenopsis* are narrower than dorsal sepals of plants of 'PHA1794396'.
2. Lateral sepals of plants of the new *Phalaenopsis* are white in color whereas lateral sepals of plants of 'PHA1794396' are yellow green in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA379819' grown in a container.

Figure 2:
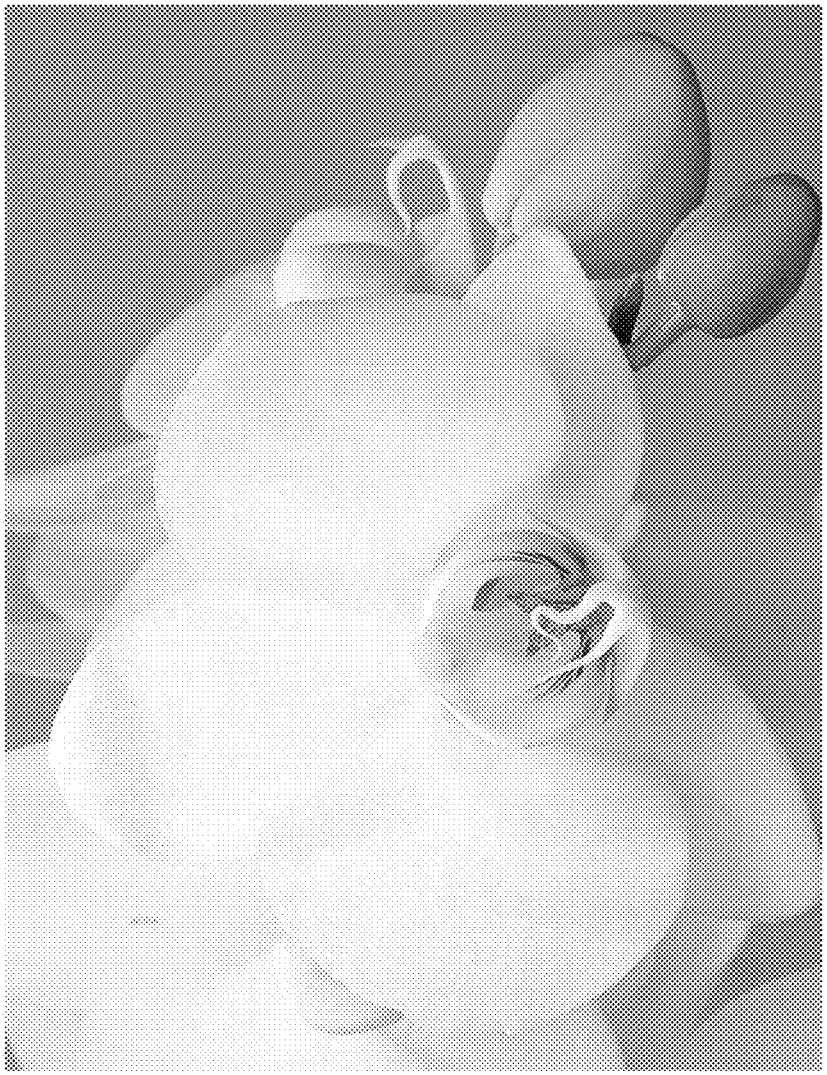

The photograph on the second sheet (FIG. 2) is a close-up view of a typical flower and flower buds of 'PHA379819'.

DETAILED BOTANICAL DESCRIPTION

The aforementioned photographs and following observations and measurements describe plants grown during the spring in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification:

*Phalaenopsis hybrida* 'PHA379819'.

Parentage:

*Female, or seed, parent*.—Proprietary breeding selection of *Phalaenopsis hybrida* identified as code number 12-051399-0002, not patented.

*Male, or pollen, parent*.—Proprietary breeding selection of *Phalaenopsis hybrida* identified as code number 13-057233-0001, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; compact and upright plant habit with typically two inflorescences developing per plant, each inflorescence with numerous flowers; monopodial; moderately vigorous growth habit and moderate growth rate.

*Plant height, substrate level to top of foliar plane*.—About 18.5 cm.

*Plant height, substrate level to top of floral plane*.—About 31.3 cm.

*Plant diameter or spread*.—About 24.3 cm.

Leaf description:

*Arrangement and quantity*.—Distichous, simple; sessile; about six to eight fully-developed leaves per plant.

*Length*.—About 15.7 cm.

*Width*.—About 5.6 cm.

*Aspect*.—Erect to semi-erect.

*Shape*.—Oblanceolate; slightly carinate.

*Apex*.—Unequal broadly acute.

*Base*.—Sheathing. Sheath length: About 1.6 cm. Sheath width: About 1.3 cm. Sheath color: Close to 143C.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to a blend of 143A and 146A; narrow marginal edges, close to 144A. Developing leaves, lower surface: Close to 146B. Fully expanded leaves, upper surface: Close to a blend of 143A and 146A; narrow marginal edges, close to 144A; venation, close to 137C. Fully expanded leaves, lower surface: Close to 144A and 144B; venation, close to 144B.

Inflorescence description:

*Appearance and flowering habit*.—Showy zygomorphic flowers arranged on axillary simple or branched racemes; typically two inflorescences develop per plant; each inflorescence with about 24 flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about twelve weeks on the plant; flowers not persistent.

*Inflorescence length* (*lowermost flower to inflorescence apex*).—About 24.4 cm.

*Inflorescence width*.—About 17.3 cm.

*Flower buds*.—Height: About 1.5 cm. Diameter: About 1.1 cm by 1.3 cm. Shape: Broadly ovate. Color: Close to 145B; apex, close to N144D.

*Flower size*.—About 6.9 cm (vertical) by 7.2 cm (horizontal).

*Flower depth*.—About 2.7 cm.

*Petals, quantity and arrangement*.—Three, two lateral petals and one center petal transformed into a labellum.

*Lateral petals*.—Length: About 3.5 cm. Width: About 3.8 cm. Shape: Reniform. Apex: Obtuse to broadly retuse. Margin: Entire; not undulate. Texture and luster, upper and lower surfaces: Smooth, glabrous; moderately velvety; matte. Color: When opening, upper surface: Close to NN155B. When opening, lower surface: Close to 155C; towards the center, close to 157C. Fully opened, upper and lower surfaces: Close to NN155D; color does not change with subsequent development.

*Labella*.—Appearance: Three-parted with two lateral lobes and a central lobe; overall shape, broadly cordate to reniform. Length, lateral lobes: About 2 cm. Width, lateral lobes: About 1.5 cm. Length, central lobe: About 1.7 cm. Width, central lobe: About 3.5 mm to 21 mm. Length, cirrhose tips: About 1 cm. Shape, lateral lobes: Broadly obovate. Shape, central lobe: Broadly rhomboidal with a slightly elongated apex. Apex, lateral lobes: Obtuse. Apex, central lobe: Bluntly acute with two cirrhose apices, curled and pointing upwards and backwards. Margins, lateral and central lobes: Entire. Texture and luster, lateral and central lobes, upper and lower surfaces: Smooth, glabrous; moderately velvety; matte. Callosities: Located at the base of the labellum and attachment point of the lateral petals; about 4 mm in length, about 5.5 mm in width and about 5 mm in height. Color: When opening, upper surface: Lateral lobes: Close to NN155D; at the base, axial stripes, close to 186A; lower margins, close to 154B. Central lobe: Close to NN155C; along the main vein, tinged with close to 155A; towards the base, close to 154B; at the base, close to NN155A with radial stripes, close to 181B; narrow distal margins, close to 174B; cirrhose apices, close to NN155C. Callosities: Close to 2B; towards the apex, close to 3A with fine dots and stripes, close to 182C. When opening, lower surface: Lateral lobes: Close to NN155D; lower margins, close to 154B. Central lobe: Close to NN155C; along the main vein, tinged with close to 157B and 157C; towards the base, close to 154B; at the base, close to 155A; narrow distal margins, close to 170A and N170; cirrhose apices, close to NN155C. Fully opened, upper surface: Lateral lobes: Close to NN155D; at the base, axial stripes, close to 185B; lower margins, close to 7B and 7C. Central lobe: Close to NN155D; towards the base, close to 8A; at the base, close to NN155A with radial stripes, close to 181B; narrow distal margins, close to 163A; cirrhose apices, close to NN155D. Callosities: Close to 13B; towards the apex, close to 16A with fine dots and stripes, close to 183C. Fully opened, lower surface: Lateral lobes: Close to NN155D; lower margins, close to 7C. Central lobe: Close to NN155D; along the main vein, tinged with close to 155A; towards the base, close to 4A; at the base, close to 155A; narrow distal margins, close to 163B; cirrhose apices, close to NN155D.

*Sepals*.—Quantity and arrangement: Three, one upper dorsal sepal and two lower lateral sepals. Length, dorsal sepal: About 3.7 cm. Width, dorsal sepal: About 2.6 cm. Length, lateral sepals: About 3.7 cm. Width, lateral sepals: About 2.1 cm. Shape, dorsal sepal: Ovate-elliptic. Shape, lateral sepals: Ovate. Apex, dorsal sepal: Obtuse. Apex, lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to 157D. When opening, lower surface: Close to 145C; towards the apex and margins, close to 157B. Fully opened, upper surface: Close to NN155D. Fully opened, lower surface: Close to NN155C. Color, lateral sepals: When opening, upper surface: Close to 157C; towards the lower margins, close to 157B. When opening, lower surface: Close to 145D; towards the lower margins, close to 145C. Fully opened, upper surface: Close to NN155D; towards the lower margins, close to NN155B. Fully opened, lower surface: Close to NN155C; towards the lower margins, close to NN155A.

*Peduncles*.—Length: About 31.1 cm. Diameter: About 5 mm. Strength: Strong. Aspect: Upright to outwardly arching. Texture and luster: Smooth, glabrous; matte. Color: Close to 148B; densely covered with fine dots, close to 145B and 152A.

*Pedicels*.—Length: About 2.8 cm. Diameter: About 3 mm. Strength: Moderately strong. Aspect: About 50° from peduncle axis. Texture and luster: Smooth, glabrous; matte. Color: Close to 144D; distal end, close to 157D; proximal end, close to 144A and 144B.

*Reproductive organs*.—Androecium: Column length: About 7 mm. Column width: About 5 mm. Column color: Close to NN155C. Pollinia quantity: Two. Pollinia diameter (per two pollinia): About 2.75 mm. Pollinia color: Close to 21A. Gynoecium: Stigma length: About 3 mm. Stigma width: About 4 mm. Stigma shape: Reniform. Stigma color: Close to 155C. Ovary length: About 7 mm. Ovary diameter: About 1 mm. Ovary color: Close to 150A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA379819' as herein illustrated and described.

* * * * *